US010285813B2

(12) United States Patent
Kocaturk

(10) Patent No.: US 10,285,813 B2
(45) Date of Patent: May 14, 2019

(54) TENSIONING DEVICE AND METHODS FOR USE

(71) Applicant: The United States of America, as represented by the Secretary, Department of Health and Human Services, Washington, DC (US)

(72) Inventor: Ozgur Kocaturk, Rockville, MD (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 231 days.

(21) Appl. No.: 14/956,238

(22) Filed: Dec. 1, 2015

(65) Prior Publication Data

US 2016/0081798 A1     Mar. 24, 2016

Related U.S. Application Data

(62) Division of application No. 13/254,160, filed as application No. PCT/US2010/026245 on Mar. 4, 2010, now abandoned.

(60) Provisional application No. 61/157,267, filed on Mar. 4, 2009.

(51) Int. Cl.
*A61B 17/04* (2006.01)
*A61F 2/24* (2006.01)
(Continued)

(52) U.S. Cl.
CPC .......... *A61F 2/246* (2013.01); *A61B 17/0487* (2013.01); *A61F 2/2445* (2013.01);
(Continued)

(58) Field of Classification Search
CPC ........ A61B 17/0487; A61B 2017/0409; A61B 2017/0451; A61B 2017/0496; F16G 11/04
See application file for complete search history.

(56) References Cited

U.S. PATENT DOCUMENTS 2,856,933 A   10/1958 Hildebrand et al.
4,156,574 A    5/1979 Boden
(Continued)

FOREIGN PATENT DOCUMENTS

EP   0 591 991   4/1994
EP   1 683 492   7/2006

OTHER PUBLICATIONS

International Search Report from International Application No. PCT/US2010/026245 dated May 26, 2010.
(Continued)

*Primary Examiner* — Robert A Lynch
(74) *Attorney, Agent, or Firm* — Klarquist Sparkman, LLP

(57) ABSTRACT

A tensioning device is provided comprising a locking device. The locking device comprises a locking enclosure comprising a groove and a locking pin comprising teeth. The tensioning device further comprises a suture comprising first and second portions. The first and second portions of the suture and the locking pin are positioned within the groove of the locking enclosure and the locking pin is movable within the groove between a first, outer position in which the teeth are disengaged from the suture so that the locking device is movable along the first and second portions of the suture and a second, inner position in which the teeth are engaged with the suture so that the locking device is not movable along the suture. Methods for treating mitral valve regurgitation are also provided.

9 Claims, 7 Drawing Sheets

(51) Int. Cl.
 F16G 11/10 (2006.01)
 F16G 11/14 (2006.01)
(52) U.S. Cl.
 CPC .......... *A61F 2/2466* (2013.01); *F16G 11/101* (2013.01); *F16G 11/106* (2013.01); *F16G 11/14* (2013.01); *A61B 2017/0409* (2013.01); *A61B 2017/0451* (2013.01); *A61B 2017/0496* (2013.01)

(56) References Cited

U.S. PATENT DOCUMENTS

| | | | |
|---|---|---|---|
| 4,250,653 | A | 2/1981 | Davies |
| 5,562,689 | A * | 10/1996 | Green ................ A61B 17/0401 24/115 M |
| 5,572,770 | A | 11/1996 | Boden |
| 5,894,639 | A | 4/1999 | Boden et al. |
| 7,574,779 | B2 | 8/2009 | Takahashi |
| 2005/0143762 | A1 | 6/2005 | Paraschac et al. |
| 2007/0276437 | A1 * | 11/2007 | Call ................... A61B 17/0487 606/232 |
| 2008/0167606 | A1 | 7/2008 | Dann et al. |
| 2008/0228267 | A1 * | 9/2008 | Spence ............. A61B 17/0401 623/2.36 |
| 2008/0300629 | A1 | 12/2008 | Surti |
| 2009/0171378 | A1 | 7/2009 | Coe et al. |

OTHER PUBLICATIONS

Written Opinion of the International Search Report from International Application No. PCT/US2010/026245 dated May 26, 2010.

\* cited by examiner

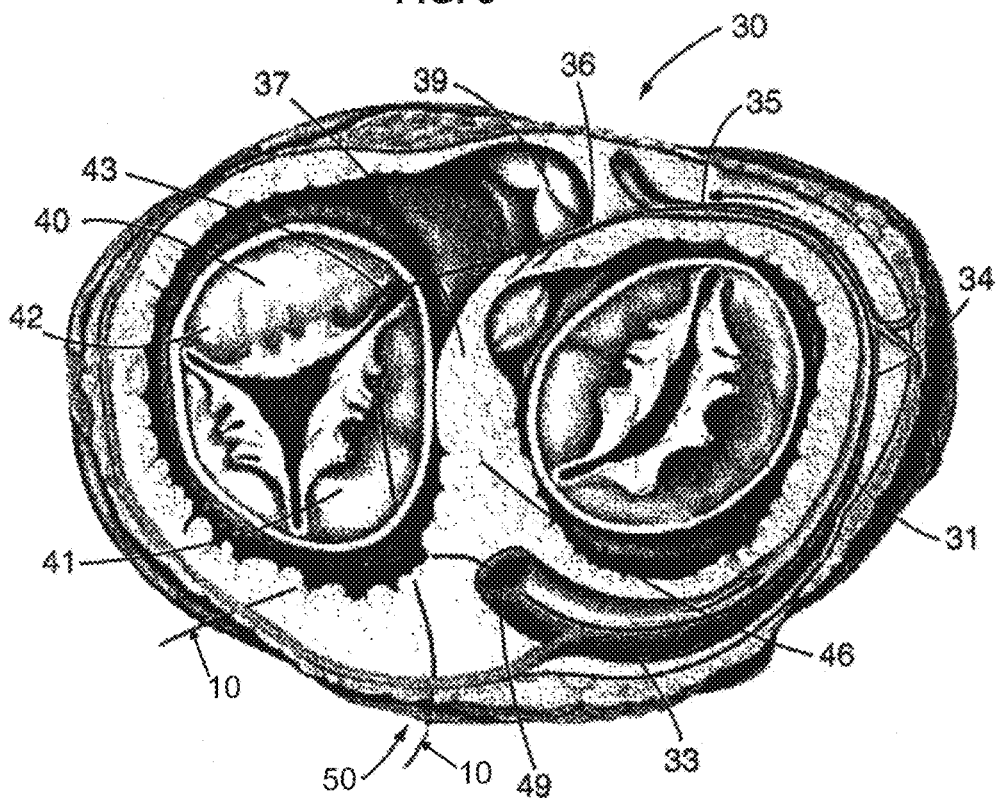

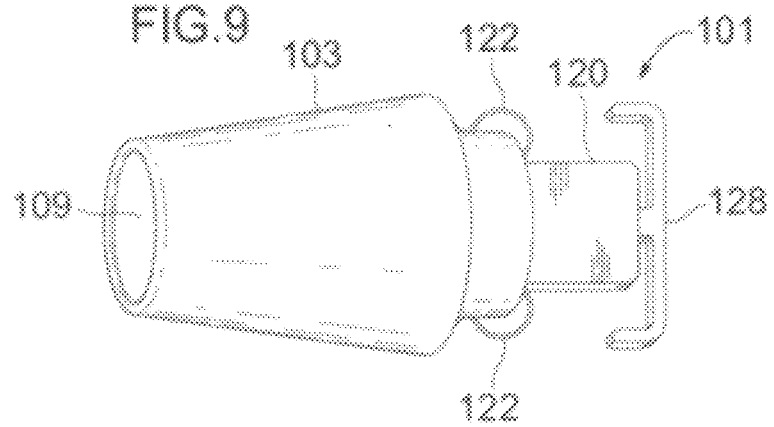
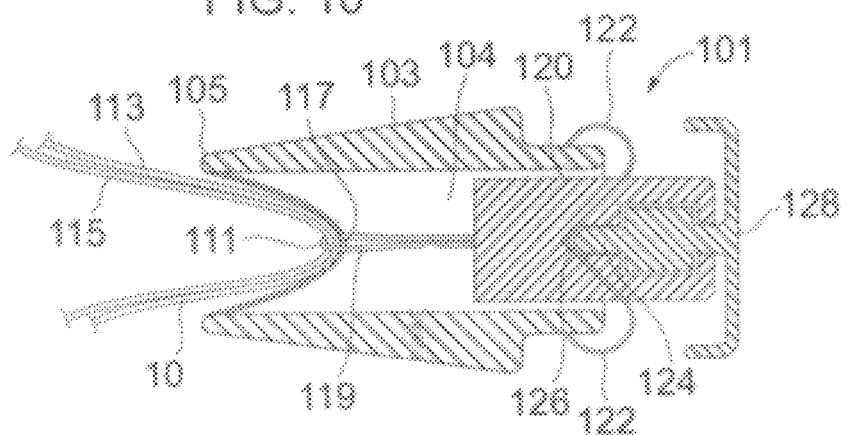
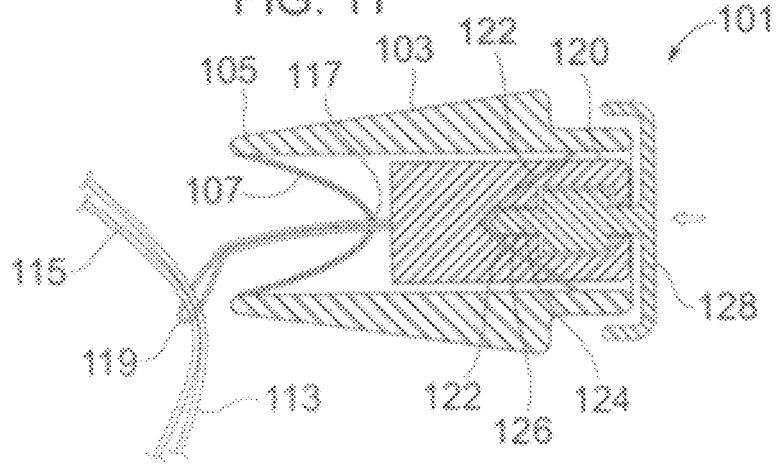

TENSIONING DEVICE AND METHODS FOR USE

CROSS REFERENCE TO RELATED APPLICATIONS

This is a divisional of U.S. application Ser. No. 13/254,160, filed Aug. 31, 2011, which is the U.S. National Stage of International Application No. PCT/US2010/026245, filed Mar. 4, 2010, which was published in English under PCT Article 21(2), which in turn claims the benefit of priority of U.S. Provisional Application No. 61/157,267, filed Mar. 4, 2009. Each of these prior applications is incorporated by reference herein in its entirety.

BACKGROUND OF THE INVENTION

Mitral valve regurgitation is a cardiac valve disorder characterized by the abnormal leakage of blood from the left ventricle to the left atrium due to inadequate coaptation of the mitral valve leaflets. Normal blood flow passes from the left atrium to the left ventricle. Mitral valve regurgitation, however, is characterized by leakage of the blood backwards, i.e., from the left ventricle to the left atrium. Mitral valve regurgitation may be caused by any of a variety of injuries or diseases of the cardiovascular system, for example, myocardial infarction, cardiomyopathy, cardiac fibrosis, ischemia, hypertension, myxomatous degeneration of the valve, myocarditis, and enlargement of the mitral annulus and/or left ventricular cavity. If left untreated, mitral valve regurgitation can weaken the heart over time and lead to heart failure.

In spite of considerable research into mitral valve regurgitation, there is a need in the art for improved devices and methods for treating and/or preventing mitral valve regurgitation.

SUMMARY

In one embodiment, an adjustable tensioning device that includes a locking device is provided. The locking device comprises a locking enclosure comprising a groove and a locking pin comprising teeth. At least two portions of suture (e.g., first and second portions) and the locking pin are positioned within the groove of the locking enclosure. The locking pin is movable within the groove between a first, outer position in which the teeth are disengaged from the suture so that the locking device is movable along the first and second portions of the suture and a second, inner position in which the teeth are engaged with the suture so that the locking device is not movable along the suture.

In another embodiment, a method for treating mitral valve regurgitation includes forming a loop of suture around a mitral valve annulus. The method includes coupling the suture with a locking device comprising a locking enclosure and a locking pin. The locking pin comprises teeth that can engage the first and second ends of the suture after the first and second ends are passed through the locking enclosure and the locking pin is inserted into the locking enclosure. The method also comprises adjusting tension of the suture to reduce mitral valve annulus size by moving the locking device along the suture. The method further comprises locking tension of the suture around the mitral valve annulus by moving the pin from an outer position in which the teeth are disengaged from the suture and the locking device is movable along the suture to an inner position in which the teeth are engaged with the suture and the locking device is not movable along the suture.

In another embodiment, a locking device for securing two portions of suture together is provided. The locking device comprises an enclosure having an internal cavity and a distal opening at a distal end of the enclosure. A moveable member having a distal end is positioned at least partially within the internal cavity, such that it is moveable within the cavity between a first position and a second position. A snare member having a loop that extends from the distal end of the moveable member is also provided. The loop can extend at least partially out of the distal opening of the enclosure. An effective diameter of the loop is the portion of the loop that extends out of the opening, and the effective diameter of the loop when the moveable member is in the first position is smaller than the effective diameter of the loop when the moveable member is in the second position. In some embodiments, the effective diameter of the loop when the moveable member is in the first position is smaller than the combined diameter of two portions of suture that are to be secured by the locking device. In other embodiments, a biasing member can extend from the moveable member and at least partly engage the enclosure to restrict movement of the moveable member from the first position to the second position. The biasing member can comprise one or more curved Nitinol arms. In other embodiments, the moveable member can comprise an internal cavity and a portion of a handle member can be moveable mounted within the internal cavity. By moving the handle member in the distal direction, the portion of the handle member in the internal cavity can release the biasing member and permit movement of the moveable member from the first position to the second position.

In another embodiment, a method for treating mitral valve regurgitation includes the acts of forming a loop of suture around a mitral valve annulus and positioning two portions of the suture through a loop of a snare member. The snare member extends from a distal opening in an enclosure and is mounted to a distal end of a moveable member that is mounted at least partially within a cavity of the enclosure. Tension of the suture can be adjusted to reduce mitral valve annulus size by moving the loop of the snare member along the suture. Tension of the suture around the mitral valve annulus can then be locked by moving the moveable member within the cavity and causing a portion of the loop to move into the enclosure through the distal opening, thereby reducing an effective diameter of the portion of the loop that extends out of the distal opening.

BRIEF DESCRIPTION OF THE SEVERAL VIEWS OF THE DRAWING(S)

FIG. 5 is a lateral cross section of a human heart viewed from the apex of the heart showing a pathway of a suture through the heart for securement by a tensioning device.

FIG. 6 is a longitudinal cross section of a human heart showing the pathway of a suture through the heart for securement by a tensioning device.

FIG. 9 is a perspective view of another embodiment of a tensioning device.

FIG. 10 is a cross-sectional view of a first position of the tensioning device shown in FIG. 9, shown in a configuration where two portions of suture are captured by a loop member and secured together.

FIG. 11 is a cross-sectional view of a second position of the tensioning device shown in FIG. 9, shown in a configuration where two portions of suture are captured by a loop member, but not secured together.

DETAILED DESCRIPTION

Figure 1:
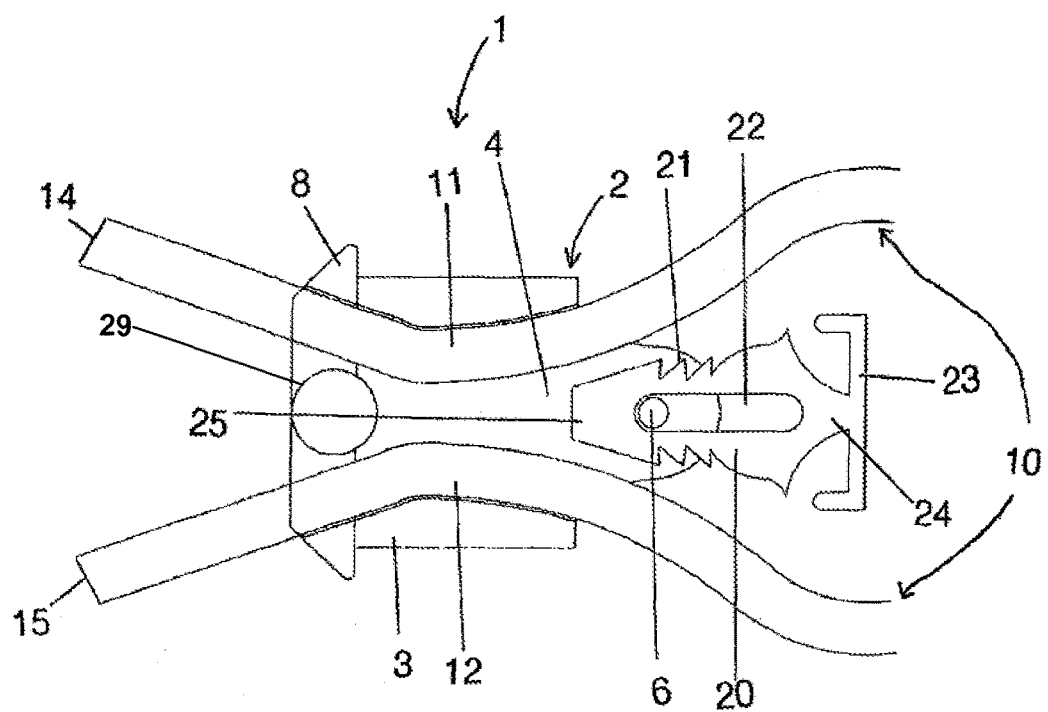
FIG. 1 is a cutaway view of a tensioning device according to one embodiment.

The devices and methods according to the following embodiments may be used to apply tension to a suture in any medical procedure. In this regard, the devices and methods disclosed herein may be used, for example, to hold a surgical opening closed or to treat or prevent any medical condition in a host. For example, the devices and methods disclosed herein may be used to treat cardiovascular conditions (e.g., mitral valve regurgitation), endoscopic surgeries, and/or orthopedic conditions. The devices and methods disclosed herein can advantageously treat or prevent mitral valve regurgitation in a host by reducing the circumference of the mitral valve annulus and enhancing mitral leaflet coaptation by applying circumferential tension. The devices and methods disclosed herein can also make it possible to treat cardiovascular conditions in a host percutaneously, thereby advantageously avoiding open-heart surgery. In addition, the devices and methods disclosed herein can advantageously allow for the readjustment and maintenance of tension. As described in more detail herein, the combination of a suture and locking device can function as a cerclage to adjust the diameter of an annulus of the body.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the various methods disclosed herein can provide any amount of any level of treatment or prevention of disease or injury in a host. Furthermore, the treatment or prevention provided by the various methods disclosed herein can include treatment or prevention of one or more conditions or symptoms of the disease, e.g., mitral valve regurgitation, being treated or prevented. Also, for purposes herein, "prevention" can encompass delaying the onset of the disease, or a symptom or condition thereof.

The host referred to in the inventive methods can be any host. Preferably, the host is a mammal. The term "mammal" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

The described methods, systems, and apparatus should not be construed as limiting in any way. Instead, the present disclosure is directed toward all novel and nonobvious features and aspects of the various disclosed embodiments, alone and in various combinations and sub-combinations with one another. The disclosed methods, systems, and apparatus are not limited to any specific aspect, feature, or combination thereof, nor do the disclosed methods, systems, and apparatus require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods, systems, and apparatus can be used in conjunction with other systems, methods, and apparatus.

In a first embodiment, the tensioning device 1 comprises a locking device 2 that includes a locking enclosure 3 and a moveable locking pin 20. As illustrated in FIG. 1, tensioning device 1 can receive two portions 11, 12 of a suture 10 at least partially within enclosure 3 of locking device 2. The moveable locking pin 20 can also be received at least partially within locking enclosure 3 to secure the two portions of the suture 10 together, thereby forming a loop of suture or otherwise locking two suture elements together. Locking enclosure 3 can comprises a cavity or groove 4 into which the two portions of suture 10 and the moveable locking pin 20 can be received. If two ends of a single piece of suture 10 are being secured together using locking device 2, a first end 14 and second end 15 can be passed through groove 4 and received into locking device 2 as shown in FIG. 1. Locking enclosure 3 can comprises a separator 29 positioned at the distal end of locking enclosure to allow first and second ends 14, 15 of suture 10 to be separated from one another. Separator 29 can comprise, for example, a post between first and second sides of locking enclosure 3.

If desired, moveable locking pin 20 can be moveably mounted or secured to locking enclosure 3. To secure the two elements, a portion of locking enclosure 3 can be engageable with a portion of locking pin 20 to keep locking pin 20 connected to locking enclosure 3. For example, locking enclosure 3 can comprise a post 6, which is received into a channel 22 of locking pin 20. Moveable locking pin 20 can move relative to locking enclosure 3 along the length of channel 22 to allow locking pin 20 to move from an unlocked (unsecured) position (FIG. 1) to a locked position where locking pin 20 is fully engaged with the two portions 14, 15 of suture 10.

In the embodiment shown in FIG. 1, post 6 is formed with or connected to locking enclosure 3 and is engageable with channel 22 of locking pin 20. Alternatively, the locking enclosure may include a channel engageable with a post on the locking pin to keep the locking pin in place within the groove of the locking enclosure. In both of these configurations, locking pin 20 is movable along the longitudinal axis of the locking enclosure 3 within a range permitted by the post 6 of the locking enclosure 3 (or the locking pin) engaged with the channel 22 of the locking pin 20 (or the locking enclosure).

Locking enclosure 3 can also comprise a flange 8 positioned at an end of locking enclosure 3. As described in more detail below, flange 8 or another similar element, can provide a surface for applying pressure against locking enclosure 3 from the distal end (i.e., towards locking pin 20).

Figure 2:
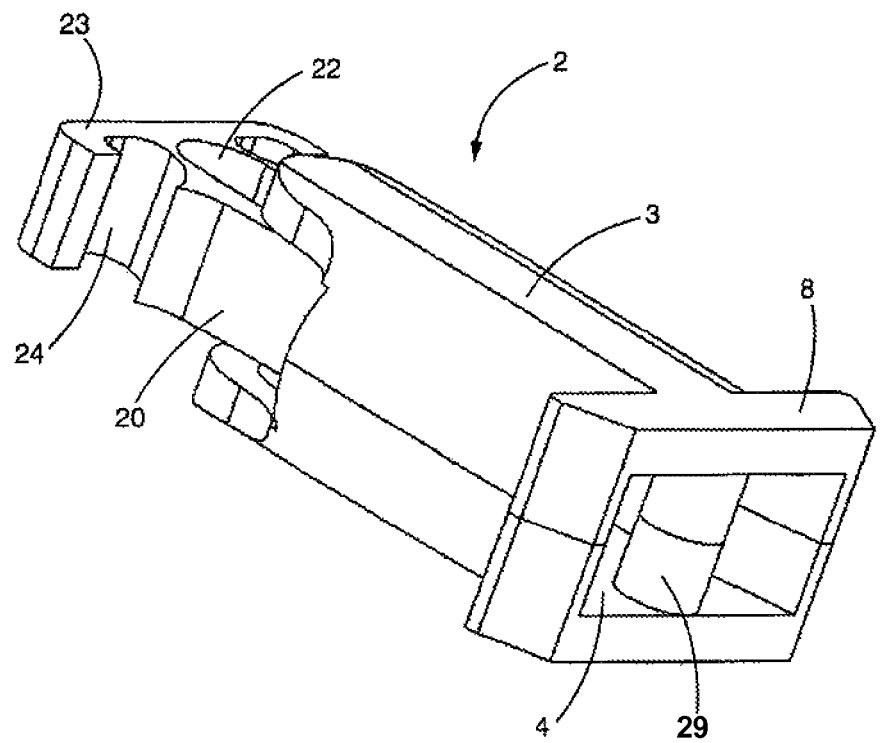
FIG. 2 is a perspective view of the tensioning device of FIG. 1.

Locking pin 20 can comprise any one or more of a tooth, a post, a head, a neck, and a tip. Preferably, the locking pin comprises a plurality of teeth, a head, a neck, and a tip. In the embodiments shown in FIGS. 1 and 2, the illustrated locking pin 20 can comprise teeth 21, a head 23, a neck 24, and a tip 25. As shown in FIG. 1, locking pin 20 preferably has a tapered width and as locking pin 20 moves into groove or cavity 4, the widest portion of locking pin 20 presses against the first and second portions 11, 12 of suture 10 to secure the suture 10 within groove or cavity 4 of locking enclosure 3.

Thus, teeth 21 of locking pin 20 are configured to engage suture 10 upon movement of locking pin 20 into groove or cavity 4 of locking enclosure 3. Teeth 21 can be any structure or structures that extend from a surface of the locking pin to engage with portions of suture to capture and secure the portions of suture within the locking device. The teeth are preferably positioned at an angle so that when the teeth engage with the two portions 11, 12 of suture 10, the teeth 21 and the geometry of groove 4 allow locking pin 20 to move even further inside groove 4 to increase the locking force and, at the same time, resist movement of locking pin 20 out of groove 4. Accordingly, the locking device 2 provides a safety mechanism that restricts locking pin 20 from moving toward a disengaged position out of groove 4 that could lead to an undesirable decrease of the suture tension over time.

Locking pin 20 is moveable within groove 4 of locking enclosure 3 between a first, outer position in which teeth 21 of locking pin 20 are disengaged from suture 10 and a second, inner position in which teeth 21 are engaged with suture 10. With reference to FIG. 1, locking pin 20 may be positioned in a first, outer position in which teeth 21 of the locking pin 20 are disengaged from both first 11 and second 12 portions of suture 10. When locking pin 20 is in the first, outer position in which the teeth are disengaged from the suture, locking device 2 is moveable along the suture.

To lock or secure the locking device 2 to suture 10, locking pin 20 may be positioned in a second, inner position in which teeth 21 of locking pin 20 are engaged with both first 11 and second 12 portions of the suture. When locking pin 20 is in the second, inner position in which teeth 21 are engaged with suture 10, locking device 20 is not moveable along the suture. Accordingly, in the first position, locking device 20 is moveable relative to suture 10 and can be moved along the suture to adjust or change the size (e.g., diameter) of the suture loop to adjust the tension in the suture loop, and, in the second position, locking device 20 is not moveable relative to suture 10 and the suture loop has a fixed size (e.g., diameter).

Locking device 2, including the locking pin and the locking enclosure, may comprise any one or more biocompatible materials that are rigid enough to maintain structural integrity under tension and which may be enable visualization of the locking device within the body by, e.g., magnetic resonance imaging (MRI), x-ray, fluoroscopy, and/or angiography. In some embodiments, the locking device comprises a biocompatible metal such as, e.g., any one or more of stainless steel (e.g., 304 or 316 (medical grade) stainless steel), cobalt alloy (e.g., nickel-cobalt alloy, cobalt chromium), nickel-titanium alloy (e.g., nitinol), titanium, tantalum, tungsten, gold, platinum, and MP35N alloy. In some embodiments, the locking device comprises a biocompatible metal coated with a polymer to increase biocompatibility, e.g., an anticoagulant polymer coating. In a preferred embodiment, the locking device comprises biocompatible titanium coated with biocompatible polymer. In some embodiments, the locking device comprises a biocompatible polymer, such as, e.g., polyetherimide (e.g., Ultem®), polyetheretherketone (PEEK), and polyamide. In some embodiments, the biocompatible polymer is coated with a material that enables visualization within the body, such as, for example, any one or more of the biocompatible metals described herein.

As noted above, the materials of the locking device can be selected to provide sufficient visualization using MRI. It may also be desirable to include "active" visualization structures that are even more visible using MRI. For example, the locking device can comprise receiver coils on an outer or inner surface of the device to facilitate imaging and tracking the location of the locking device inside the body.

As discussed above, the tensioning device can secure one or more sutures together For example, as shown in FIG. 1, tensioning device 1 secures first 11 and second 12 portions of suture 10. The suture may comprise any suitable material, preferably a biocompatible material. For example, the suture may comprise any one or more of silk, polypropylene (e.g., Prolene®), polyester (e.g., Dacron®), and nylon. In one embodiment, the suture may comprise one or more markers that permit visualization of the suture within the body. For example, the markers may comprise any biocompatible material that enables visualization within the body, such as any one or more of the coated or uncoated metallic materials described herein. In addition, various coatings can be applied to the sutures to facilitate movement of the locking device over the portions of suture received in groove 4, such as a thin polytetrafluoroethylene (PTFE) coating. The sutures can also comprise hollow shafts or other such members with internal lumen or openings.

Methods for treating mitral valve regurgitation can include the use of tensioning devices as described herein to adjust forces applied to the mitral valve. For example, the method can comprise positioning a suture within the heart of a host to form a loop of suture around the mitral valve annulus and adjusting tension of the suture using a tensioning device as described herein to reduce the size of the mitral valve annulus. Preferably, a guidewire (e.g., annuloplasty wire) is first positioned within the heart and later replaced with suture.

Figure 8:
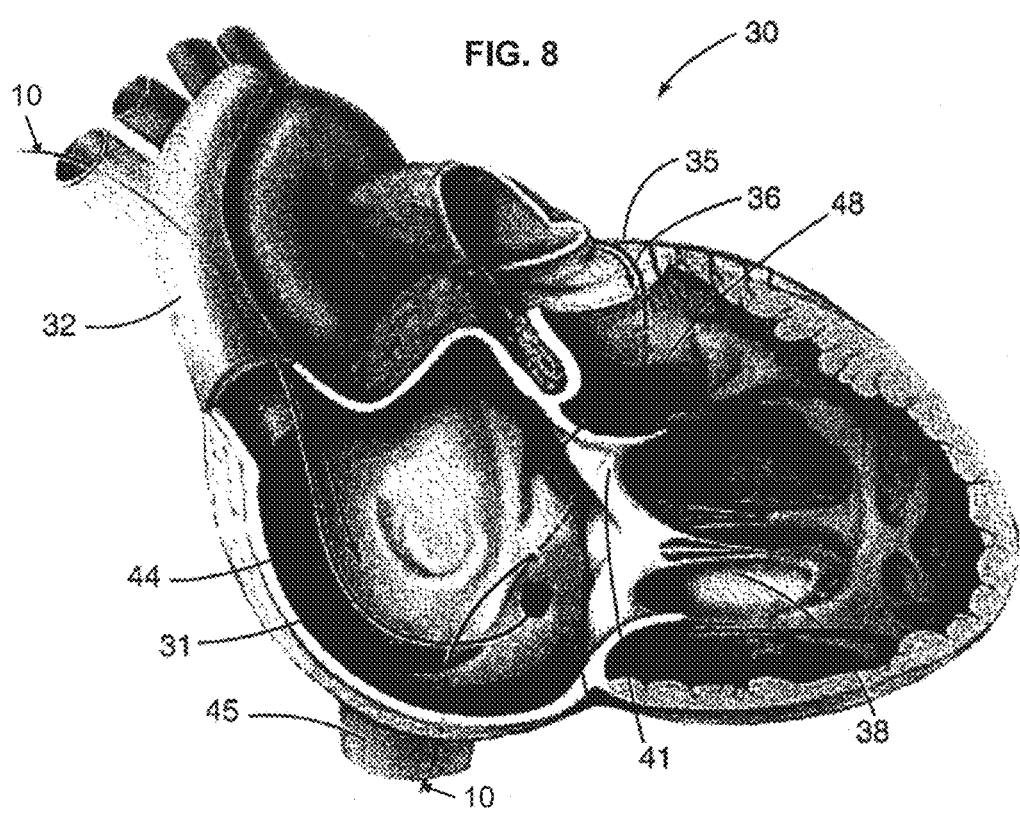
FIG. 8 is a longitudinal cross section of a human heart showing the pathway of a suture through the heart for securement by a tensioning device.

In the illustrated embodiment, a suture can be passed through a coronary sinus, a proximal great cardiac vein, a first septal vein, and a right chamber of the heart. As shown in FIGS. 6 and 8, the suture 10 can enter the heart 30 through the superior vena cava 32. The suture 10 can follow a pathway 31 from the superior vena cava 32 passing through the coronary sinus 33, the proximal great cardiac vein 34, the anterior interventricular vein 35, and the first septal vein 36 towards the intact ventricular septum (IVS) 46. The method comprises passing a suture through a segment of myocardium (in the direction shown by arrow 50) to enter a right heart chamber (either the right ventricle 38 or the right atrium 44).

The suture can follow a right ventricular (RV) pathway through the heart. The method according to this embodiment comprises passing the suture 10 from the first septal vein into the right ventricle. As shown in FIGS. 5 and 6, the suture 10 can pass from the first septal vein 36 across a short segment of myocardium 37 into the right ventricular outflow tract (RVOT) 48 of the right ventricle 38. The method further comprises passing the suture 10 from the right ventricle through the intersection of the anterior cusp and the septal cusp of the tricuspid valve, and passing the suture 10 into the right atrium. The suture 10 can exit the RVOT 48 below the pulmonary valve 39, pass through the intersection 43 of the anterior cusp 40 and septal cusp 41 of the tricuspid valve 42, and reenter the right atrium 44. The suture 10 can exit the heart through the inferior vena cava 45.

Figure 7:
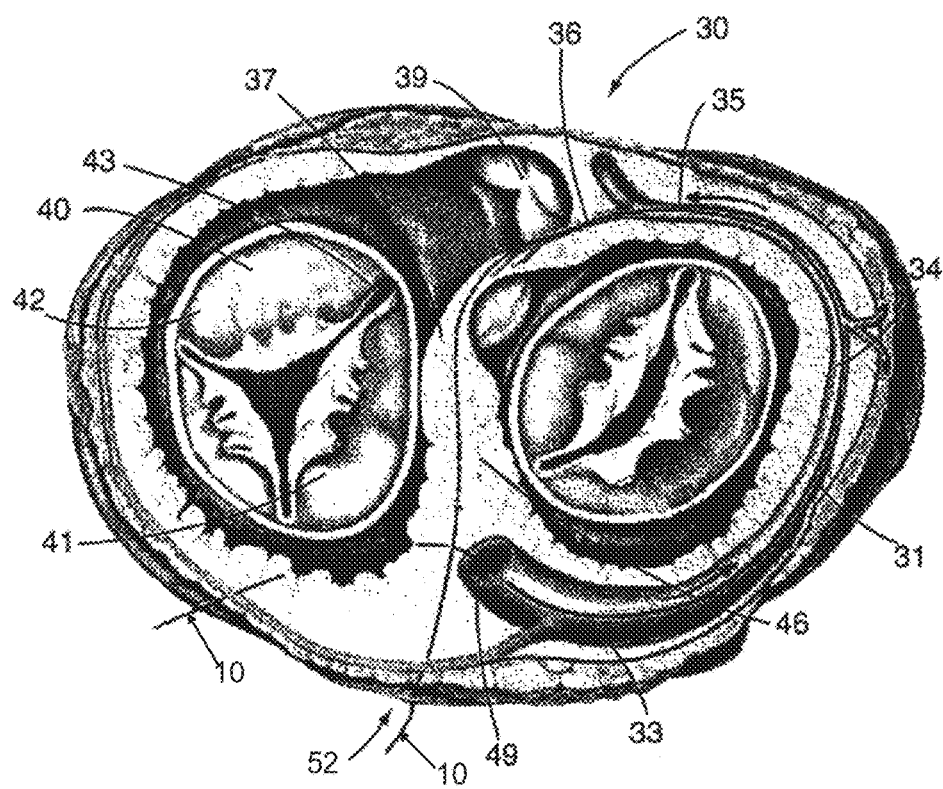
FIG. 7 is a lateral cross section of a human heart viewed from the apex of the heart showing a pathway of a suture through the heart for securement by a tensioning device.

In another embodiment, the suture can follow a right atrial (RA) pathway through the heart. The method according to this embodiment comprises passing the suture 10 from the first septal vein into the right atrium. As shown in FIGS. 7 and 8, the suture 10 can pass from the first septal vein 36, traverse a longer distance of myocardium 37 (in the direction shown by arrow 52), and traverse the IVS 46 moving in a posterior direction and directly enter into the right atrium 44 above the coronary sinus ostium 49. The suture 10 can exit the heart through the inferior vena cava 45.

The method also comprises coupling first and second ends of the suture with a locking device, such as a locking device comprising a locking enclosure and a locking pin as described herein. The suture can be coupled with the locking device by passing the first and second ends of the suture through the locking device as described above with respect to FIG. 1. As shown in FIG. 1, the first end 14 of suture 10 can pass through groove 4 of locking enclosure 3 and exit locking enclosure 3, so that a first portion 11 of suture 10 is positioned within locking enclosure 3. Likewise, a second end 15 of suture 10 can be inserted into locking enclosure 3. As shown in FIG. 1, the second end 15 of suture 10 can pass through locking enclosure 3 and exit locking enclosure 3, so that a second portion 12 of suture 10, in addition to the first portion 11 of suture 10, is positioned within locking enclosure 3.

As described in more detail above, locking pin 20 can be inserted into locking enclosure 3 to secure the two portions 11, 12 within locking enclosure 3. Locking pin 20 can be inserted into the groove of the locking enclosure between first and second portions 11, 12, of suture 10 and moved distally into groove 4 until locking pin 20 is securely held within groove 4 between first and second portions 11, 12 of suture 10.

Figure 3:
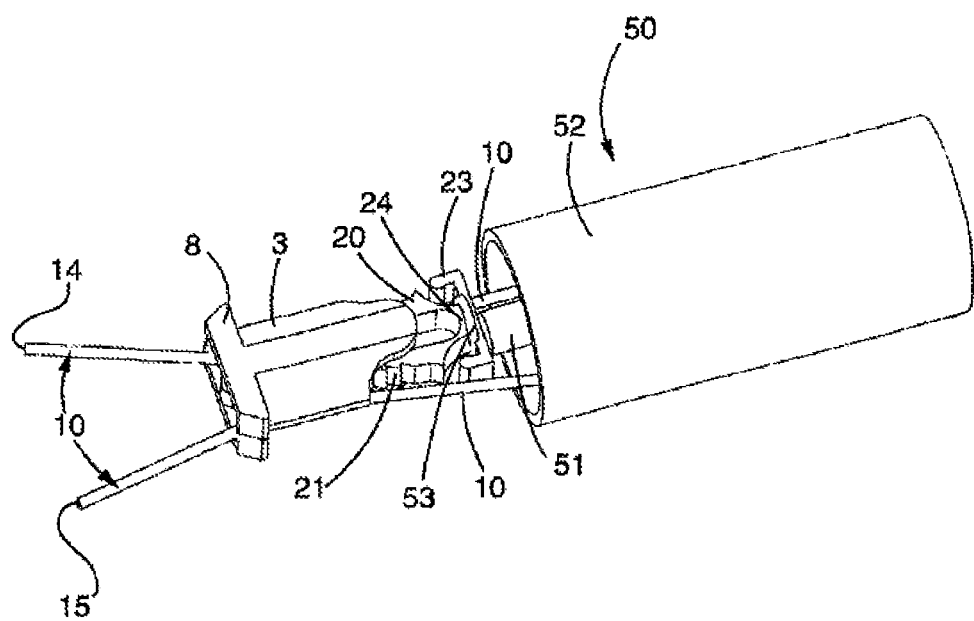
FIG. 3 is a perspective view of a tensioning device, shown with a locking pin held in an outer position by a snare catheter.

Tension in the suture can be adjusted to reduce the size of the mitral valve annulus by moving locking device 2 along the suture 10 until positioned in the desired location to provide the desired tension. A snare catheter can be used to move the locking device 2 relative to suture 10. Snare catheter can comprise a tube portion and a snare, which includes a loop. For example, as shown in FIG. 3, snare catheter 50 comprises a tube 52 and a snare 51. The snare 51 includes a loop 53.

Referring against to FIG. 3, to move the locking device along the suture 10, locking pin 20 can be placed in the first, outer position in which teeth 21 are disengaged from suture 10 so that the locking device can move relative to the suture 10. Locking pin 20 can be placed in the outer position by ensnaring head 23 of locking pin 20 with snare 51 of snare catheter 50, pulling snare 51 to pull locking pin 20 into the outer position, and clamping the snare in place to keep the ensnared locking pin 20 in the outer position.

In the embodiment shown in FIG. 3, head 23 of locking pin 20 is ensnared with snare 51 of snare catheter 50 so that loop 53 of snare 51 is positioned around neck 24 of locking pin 20 and snare 51 is pulled to place the locking pin in the outer position. A portion of the locking pin including the tip of the locking pin can remain within groove 4 of locking enclosure 3 when locking pin 20 is in the outer position. For example, in the embodiment shown in FIG. 1, the engagement of post 6 of locking enclosure 3 (or the locking pin) with channel 22 of locking pin 20 (or the locking enclosure) maintains a portion of locking pin 20, including tip 25 of locking pin 20 within groove 4 of locking enclosure 3.

Figure 4:
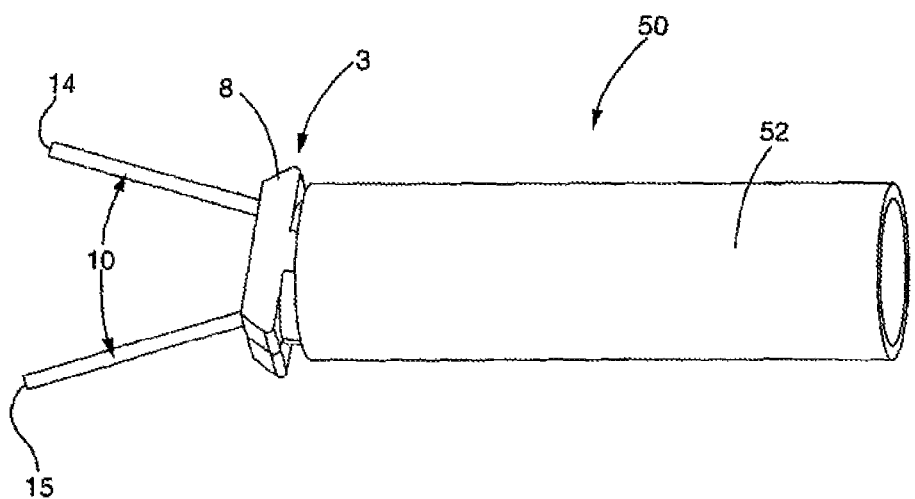
FIG. 4 is a perspective view of a tensioning device, shown with a flange of the locking enclosure abutting the tube of the snare catheter.

The method can further comprise advancing locking device 2 within tube 52 until flange 8 abuts the end of tube 52. Locking device 2 can be pulled with snare 51 to position locking device 2 within tube 52 of snare catheter 50. In the embodiments shown in FIGS. 3 and 4, locking device 2 can be pulled into tube 52 of snare catheter 50. Flange 8 provides a platform against which snare catheter 50 may push locking device 2 along suture 10. As shown in FIG. 4, flange 8 of locking enclosure 3 preferably has an outer diameter that is larger than an inner diameter of tube 52 so that as locking device 2 is advanced within snare catheter 50, flange 8 abuts the end of tube 52.

The snared locking pin can be clamped in the outer position, e.g., with a hemostat, placed on the snare catheter, thus preventing any relative movement of the locking pin during adjustment of the tension. Accordingly, in this configuration, teeth 21 of locking pin 20 remain disengaged from suture 10 and locking device 20 is moveable along suture 10.

Tension in the suture 10 can be adjusted by pushing or pulling snare catheter 50 to move locking device 2 along suture 10. To increase the tension, locking device 2 can be pushed proximally along suture 10. To decrease the tension, locking device 2 can be pulled distally along suture 10.

Once the desired amount of tension in the suture is achieved, the pin can be moved from the outer position in which the locking device is movable along the suture to the inner position in which the locking device is not movable along the suture. For example, to lock or secure locking device 2 to the suture 10, the hemostat can be released, and locking pin 20 can be pushed into the inner position by pushing snare 51 of snare catheter 50 distally. In the inner position, the teeth 21 of locking pin 20 engage the first and second portions 11, 12 of suture 10 so that locking device 2 is not moveable along suture 10. The snare catheter 50 can then be released and removed from the patient's body.

The locking device can be positioned and secured in any suitable location along the length of the suture. For the treatment of mitral valve regurgitation, the locking device is preferably placed near the coronary sinus ostium.

FIGS. 9-11 illustrate another exemplary embodiment of another tensioning device that can be used in the methods of securing one or more sutures described herein. FIG. 10 illustrates a cross-sectional view of the tensioning device 101 showing it in a locked or secured state, whereby two portions 113, 115 of a suture or other elongate members are secured together. FIG. 11 illustrates a cross-sectional view of tensioning device 101 in an unlocked or unsecured state, whereby the two portions 113, 115 of suture or other elongate members can move relative to tensioning device 101.

As shown in FIG. 9, tensioning device 101 can comprise a main body 103 and a moveable member 120. Moveable member 120 can comprises a pin-like member that can move within a cavity or groove 104 in main body 103. An opening 109 at a distal end of main body 103 allows a snare or capture member 111 that is attached to moveable member 120 to be advanced out of the main body 103. Snare member 111 can comprise a loop 119 at its distal end to capture the two portions 113, 115 of suture together.

As illustrated in FIG. 10, main body 103 can comprise a conical outer body 105 that defines opening 109. Opening 109 can comprise a tapered, inverted conical surface 107 that tapers inwardly to a smaller opening 117. Because snare member 111 is attached to moveable member 120, by moving moveable member 120 relative to main body 103, an effective diameter of loop 119 of snare member 111 can be reduced or enlarged by moving snare member 111 into or out of opening 117. The effective diameter of the loop is the diameter of loop that extends out of opening 117. Thus, by moving the loop 119 into and out of the opening 117, its effective diameter can be varied. When the effective diameter is reduced (FIG. 10), the two portions 113, 115 are secured more tightly together, and when the effective diameter is increased (FIG. 11), the two portions 113, 115 are secure less tightly together and the tensioning device can move along, or relative to, the two portions of suture.

For example, when loop 119 is in the retracted position shown in FIG. 10, loop 119 extends only a small distance out of opening 117. In this position, first portion 113 and second portion 115 are tightly secured in the loop of the snare member 111. To release the two portions 113, 115 of suture, moveable member 120 can be distally advanced into (or further into) cavity 104, as shown in FIG. 11. The distal movement of moveable member 120 relative to main body 103 also distally advances the distal end of the snare member 111 (e.g., loop 119) further out of the opening 117. Thus, by moving moveable member to the position shown in FIG. 11, tension on the two portions 113, 115 of the suture can be released, allowing the tensioning device 101 to move relative to the two portions 113, 115 of the suture.

To facilitate movement of the loop 119 over the suture portions 113, 115, loop 119 can extend from opening 117 at an angle when it is in the unsecured or unlocked configuration shown in FIG. 11. For example, as shown in FIG. 11, loop 119 can be configured and/or biased to extend at an angle from the longitudinal axis of tensioning device 101 so the application of a force along the longitudinal axis of tensioning device 101 (e.g., by pushing or pulling tensioning device 101) causes tensioning device 101 to slide easily over the portions 113, 115 of suture. As shown in FIG. 11, the angle of loop 119 relative to the longitudinal axis can be about 45-90 degrees.

The tensioning device 101 can be biased in the secured position (FIG. 10) by a biasing member 122. Biasing member 122 can comprise, for example, one or more arm members that extend at least partially across a portion of main body 103 to restrict movement of moveable member 120 into cavity 104. Upon application of sufficient force to overcome the biasing force of biasing member 122, moveable member 120 can move into cavity 104, thereby at least partially releasing the tension applied to the two portions 113, 115 of the suture. In the exemplary embodiment shown in FIGS. 9-11, biasing member 122 can comprise one or more Nitinol arm members that curve around and engage a portion of main body 103. To release the biasing force of biasing member 122, moveable member 120 can comprises a release mechanism 124. Release mechanism 124 can comprise, for example, a second pin member that is seated in a groove or cavity 126 within moveable member 120. By moving release mechanism 124 in the distal direction, release mechanism 124 engages biasing member 122, forcing it to move inward into cavity 104 along with moveable member, thereby removing the biasing force of biasing member 122 against main body 103. In the unsecured or unlocked state (FIG. 11), tensioning device 101 can be moved relative to the two portions 113, 115 of the suture to adjust the position of the tensioning device and alter tension caused by the suture in the body. Once the desired amount of tension is achieved by moving tensioning member 101 into the desired position relative to the two portions 113, 115, moveable member 120 can be released and/or pulled back out of cavity 104, thereby releasing the biasing members 122 so that they re-engage with a portion of main body 103 and once again exert a biasing force that maintains the snare member 111 in the locked position (FIG. 10).

To facilitate movement of moveable member 120, a handle or t-shaped section 128 can be provided at the proximal end of tensioning device 101. As noted above, snare member 111 is preferably attached to moveable member 120. If desired, proximal ends of snare member 111 can be secured to the handle 128 by looping or tying the wires of the snare member 111 to the handle.

The following examples further illustrate the invention but, of course, should not be construed as in any way limiting its scope.

EXAMPLE 1

This example demonstrates a method for treating mitral valve regurgitation.

Animal Preparation and Inducement of Ischemic Mitral Regurgitation

Animal procedures are approved by the National Heart, Lung, and Blood Institute Animal Care and Use Committee. A total of sixty-nine (69) swine are used in this experiment. Among them, thirty-eight (38) swine are assigned to the model of ischemic mitral regurgitation. Catheter-based myocardial infarction with intracoronary ethanol injection are employed to induce ischemic mitral regurgitation. Amiodarone (400 mg daily for 5 to 7 days) and atenolol (25 mg daily for 3 days) are given as a pre-procedural medication. Anesthesia is induced with the use of atropine, butorphanol, ketamine, and xylazine and maintained with the use of isoflurane (via inhalation) and mechanical ventilation. Animals receive intravenous heparin (50 U/kg) before transfemoral arterial and venous access.

The left circumflex (LCx) artery is primarily targeted for ethanol ablation in all animals. In order to reduce the mortality of these animals, which have a large circumflex artery, two or three sequential procedures for ethanol ablation of the proximal circumflex artery are performed in intervals of 2-4 weeks. If LCx artery ablation fails to produce ischemic mitral regurgitation during follow-up, either additional posterior-descending artery ablation (n=5) or catheter-based aortic valve perforation (perforating the valve cusp with a 0.889 mm guide wire in NCC or LCC (n=5) and 6 mm peripheral balloon dilatation of hole) is performed. Of all of the animals, two and three ethanol ablation procedures are performed in twelve (12) and seven (7) animals, respectively. A conventional, over-the-wire PTCA balloon catheter (2.5-3 mm in size) is used for the ethanol injection. Prior to ethanol injections, repetitive transient (1-2 minutes) balloon occlusion and release (1-2 minutes) at the target site is performed for 20-30 minutes in order to induce both "ischemic preconditioning" and "augmented coronary collateral flow" so that the animal can presumably tolerate the infarction better. The ethanol is then injected into the coronary artery in an amount of 1-3 mL in each procedure.

The final presence of mitral regurgitation is usually determined around 8 weeks by a follow-up MRI scan after the first infarction procedure. Among thirty-eight (38) animals, total of nineteen (19) animals (50%) die before being used in the cerclage experiment. Six (6) animals (15.8%) die during or immediately after the infarction procedure due to ventricular fibrillation. Ten (10) animals (26.3%) die during follow-up mostly due to heart failure. Three (3) animals (7.9%) die during the induction of anesthesia or during the MRI scan, which requires prolonged holding of the breath. Thirteen (13) pigs (34.2%) have mitral regurgitation of a mild degree or more (four (4) in grade I, seven (7) in grade II, two (2) in grade III, respectively), according to the criteria of the American Society of Echocardiography.

A total of fifty (50) animals, including healthy swine (n=31, 62%) and myopathic swine (n=19, 38%) are used for the mitral cerclage procedure. In the early phase of this experiment, seventeen (17) healthy swine (34%) are used for the initial technical set up, i.e., to elucidate septal vein anatomy, test technical feasibility, determine suitable imaging modality, and to design the protective device, etc. After the initial technical set up, a total of thirty-three (33) animals, including healthy swine (n=14) along with cardiomyopathic swine (n=19) undergo the cerclage procedure, and data is acquired.

Cerclage Procedure

For cerclage, 9Fr introducer sheaths are placed percutaneously into the right jugular and femoral veins, 6Fr introducer sheaths into a femoral artery, and heparin (150 units/kg) is administered.

To conduct cerclage, a transjugular balloon-tipped guiding catheter (Vueport® 8Fr, Cardima) is introduced into the coronary sinus beyond the hemiazygous branch (common in pigs), the occlusion balloon inflates, and a retrograde venogram pressurizes and opacifies the great cardiac vein and septal perforator veins. A stiff 0.3556 mm guidewire (MiracleBros 3 or 4.5 or Confianza, Asahi) is steered using a deflectable microcatheter (Venture™, St Jude Medical®) into the first basal septal perforator vein. Once a right heart chamber is entered, the guidewire is ensnared and replaced with a braided non-absorbable suture.

In twenty-two (22) animals, the cerclage is passed through the heart following a right ventricular (RV) trajectory, as follows: The guidewire exits the septal vein directly through the myocardial interstitium into the right ventricle, re-entering the right atrium along the septal tricuspid valve commissure. When the guidewire exits into RV outflow cavity, it is redirected into the pulmonary artery with use of a deflectable microcatheter and then the snare wire from the femoral vein is manipulated to capture this wire in the pulmonary artery and the wire is pulled through to the outside of heart. This also enables the wire to effectively avoid entrapment of the tricuspid subvalvular structures and easy capture of the wire. If necessary, the intramyocardial cerclage tract is dilated with a 2.0 mm coronary balloon dilatation catheter to facilitate device exchange.

Afterwards, the cerclage guidewire is snared and replaced with a suture. The suture is coupled with a locking device comprising a locking enclosure and a locking pin by passing the first and second ends of the suture through the locking enclosure and inserting the locking pin into the locking enclosure.

The tension of the suture is adjusted to reduce mitral valve annulus size by moving the locking device along the suture. Graded cerclage tension is applied interactively under imaging guidance until mitral valve regurgitation is relieved if the subject has mitral regurgitation. Most cerclage annuloplasty procedures are guided by the capabilities of XFM, which combines MRI-derived roadmaps with high-resolution X-ray fluoroscopy. XFM is used to highlight key anatomic structures, including the interventricular septum, the right ventricular moderator band, and similar trabecular structures, right ventricular outflow tract, and the planned right ventricular endocardial or right atrial endocardial re-entry point target for the cerclage guidewire. These regions of interest are manually segmented from the cardiac MRI and superimposed using external fiducial markers on the live X-ray. The regions of interest help the operator (a) direct the guidewire into a septal rather than a catastrophic right ventricular free wall vein; (b) maintain an intra-septal course during myocardial interstitial traversal; (c) select a suitable re-entry point into the desired right-sided chamber; and (d) avoid trabecular entrapment after cameral re-entry in RV cerclage.

The tension of the suture around the mitral valve annulus is locked by moving the pin from an outer position in which the locking device is movable along the suture to an inner position in which the locking device is not movable along the suture. Tension is secured with the locking device near the origin of the coronary sinus.

After experiments, animals are euthanized under general anesthesia and the position of the tensioning device is examined by necropsy.

It is observed that the tensioning device places well within the right atrium and that the tensioning device maintains the desired tension in place in 17 out of 22 animals (77.3%) in the RV cerclage group. The results are shown in Table 1.

TABLE 1

|  | RV Cerclage (n = 22) | P value |
| --- | --- | --- |
| Procedural success (n, %) | 17 (77.3%) |  |
| Procedural failure (n, %) | 5 (22.7%) | P = 0.77 |
| Wrong exit (n, %) | 4 (18.1%) |  |
| Coronary sinus (CS) dissection/thombosis (n, %) | 1 (4.5%) |  |
| Fluoroscopic time (min) | 65.2 ± 20.8 | P = 0.014 |
| Major complications | 5 (22.7%) | P = 0.34 |
| Tamponade | 0 |  |
| Unexplained blood pressure (BP) drop (n, %) under tension | 1 (4.5%) |  |
| High degree atrioventricular (AV) block (n, %) | 1 (4.5%) |  |
| Severe tricuspid regurgitation (TR) | 3 (13.6%) |  |

This example demonstrates a method for treating mitral valve regurgitation using an embodiment of the tensioning device according to the invention.

EXAMPLE 2

This example demonstrates a method of treating mitral valve regurgitation.

Eleven (11) animals are prepared and ischemic mitral regurgitation is induced as described in Example 1. The cerclage procedure described in Example 1 is followed, except that the cerclage follows a right atrial (RA) trajectory through the heart, as follows: The guidewire exits the septal vein and extends further posterior through the basal IVS into the right atrium near the coronary sinus.

It is observed that the tensioning device places well within the right atrium and that the tensioning device maintains the desired tension in place in 8 out of 11 animals (72.7%) in the RA cerclage group. The results are shown in Table 2.

TABLE 2

| | RA Cerclage (n = 11) | P value |
|---|---|---|
| Procedural success (n, %) | 8 (72.7%) | |
| Procedural failure (n, %) | 3 (27.2%) | P = 0.77 |
| Wrong exit (n, %) | 3 (27.2%) | |
| Coronary sinus (CS) dissection/thombosis (n, %) | 0 | |
| Fluoroscopic time (min) | 133.8 ± 84.8 | P = 0.014 |
| Major complications | 1 (9.1%) | P = 0.34 |
| Tamponade | 1 | |
| Unexplained blood pressure (BP) drop (n, %) under tension | 0 | |
| High degree atrioventricular (AV) block (n, %) | 0 | |
| Severe tricuspid regurgitation (TR) | 0 | |

This example demonstrates a method for treating mitral valve regurgitation using an embodiment of the tensioning device according to the invention.

EXAMPLE 3

This example demonstrates that the method for treating mitral valve regurgitation using the tensioning device according to the invention reduces the septal-lateral dimension of the mitral annulus and reduces left ventricular ejection.

The animal preparation, inducement of ischemic mitral regurgitation, and cerclage procedures of Examples 1 and 2 are followed. The septal-lateral dimension of the mitral annulus and ventricular volumes are measured. The results are shown in Table 3.

TABLE 3

| | Baseline | Tension | p value |
|---|---|---|---|
| Mitral annulus | | | |
| Septal-lateral annular diameter (cm) | | | |
| systole | 3.1 ± 0.4 | 2.5 ± 0.4 | <0.01 |
| diastole | 3.4 ± 0.6 | 2.9 ± 0.5 | <0.01 |
| Commissural Width (cm) | | | |
| systole | 2.6 ± 0.3 | 2.2 ± 0.8 | 0.41 |
| diastole | 2.6 ± 0.4 | 2.2 ± 1.0 | 0.28 |
| Cerclage diameter | | | |
| Cerclage diameter (cm) | 6.2 ± 0.8 | 4.5 ± 0.8 | <0.01 |
| Left ventricle | | | |
| diastolic LVID (cm) | 5.4 ± 0.6 | 5.3 ± 0.6 | 0.40 |
| systolic LVID (cm) | 4.7 ± 0.5 | 4.6 ± 0.7 | 0.45 |
| End-systolic volume (ml) | 106 ± 43 | 98 ± 37 | 0.22 |
| End-diastolic volume (ml) | 172 ± 55 | 158 ± 52 | 0.09 |
| Ejection fraction | 0.39 ± 0.08 | 0.34 ± 0.04 | 0.04 |

Graded tension progressively reduces the septal-lateral dimension of the mitral annulus but not significantly the commissural width. Compared with baseline, 600 g of tension reduces septal-lateral dimension approximately 20% in both systole and diastole. The septal-lateral diameter falls in linear proportion to cerclage diameter as tension is applied, $r^2=0.54$.

Ventricular volumes are reduced when tension is applied, and left ventricular ejection fraction falls in the animals with ischemic cardiomyopathy and mitral regurgitation.

This example demonstrates the method for treating mitral valve regurgitation using an embodiment of the tensioning device according to the invention reduces the septal-lateral dimension of the mitral annulus and reduces left ventricular ejection.

EXAMPLE 4

This example demonstrates that the method for treating mitral valve regurgitation using the tensioning device according to the invention does not reduce conductance-based measures of global myocardial performance.

Animal preparation, inducement of ischemic mitral regurgitation, and cerclage procedures of Examples 1 and 2 are followed and global myocardial performance is measured using conductance-catheter based methods.

Progressive tension does not reduce conductance-catheter based measures of global myocardial performance. End-systolic elastance ($E_{es}$), the slope of end-systolic pressure-volume relationship as preload changes, is 2.2±1.3 mm Hg/mL at baseline and 2.6±1.5 mm Hg/mL during tension, p<0.01.

MRI regional wall motion appears unaffected by cerclage (wall motion score index 1.54±0.12 before versus 1.56±0.16 after cerclage, p=0.76). No new late gadolinium enhancement is evident to suggest cerclage-induced myocardial infarction.

One animal of 16 with ischemic cardiomyopathy suffers high degree atrioventricular block associated with pericardial tamponade. In the others, cerclage tension induces no ECG depolarization or repolarization abnormalities.

This example demonstrates that the method for treating mitral valve regurgitation using an embodiment of the tensioning device according to the invention does not reduce myocardial performance.

EXAMPLE 5

This example demonstrates that the method for treating mitral valve regurgitation using the tensioning device according to the invention reduces mitral valve regurgitation.

The animal preparation, inducement of ischemic mitral regurgitation, and cerclage procedures of Examples 1-2 are followed.

Two thirds of animals surviving with ischemic cardiomyopathy (ejection fraction 39.2±7.6) develop significant mitral regurgitation (n=10). Successful cerclage reduces mitral valve regurgitation. A representative animal with severe ischemic cardiomyopathy is observed before and after application of cerclage tension. Black jets of dephased spins are seen regurgitating from the left ventricle. Upon applying 400 g of cerclage tension, the septal lateral annular dimension is reduced, as is the cerclage diameter. Regurgitant jets are no longer evident. Discordant cerclage and annular planes are evident and the coronary sinus does not overlap the posterior annulus.

Velocity encoded MRI is available for five animals. In these, the regurgitant fraction is reduced from 22.8±12.7% to 7.2±4.4% (p=0.04) when cerclage tension is applied. Results are shown in Table 4. Results are similar using radiocontrast ventriculography (n=10).

In preliminary experiments, three animals survive for three weeks or more after cerclage without recurrent mitral regurgitation or evident myocardial erosion.

Simultaneous tagged and color-flow MRI in an animal with mitral regurgitation that is reduced by cerclage tension is measured. Posterobasal myocardial thinning, late enhancement, and severe hypokinesis also are evident.

Mitral valve tenting area, a measure of annular dilation and subvalvular traction, is reduced after application of cerclage tension, as shown in Table 4. The degree of tenting is reduced in proportion to the reduction in cerclage diameter. By virtue of reducing septal lateral distance, the posterior displacement of the line of coaptation is reduced by cerclage.

TABLE 4

| | Baseline | Tension | p |
|---|---|---|---|
| Mitral regurgitation | | | |
| Regurgitant fraction by slice-tracking velocity-encoded MRI | 22.8 ± 12.7 | 7.2 ± 4.4 | 0.04 |
| Categorical mitral regurgitation total (Grade 1-4) | 1.7 ± 0.8 | 0.7 ± 0.5 | 0.01 |
| Mitral valve coaptation | | | |
| Mitral valve tenting area (cm$^2$) | 2.1 ± 0.5 | 1.5 ± 0.5 | 0.01 |
| Posterior displacement of line of coaptation (mm) | 25.7 ± 4.0 | 21.2 ± 4.8 | 0.01 |
| Leaflet coaptation length | 3.0 ± 2.4 | 4.8 ± 1.6 | 0.12 |

As shown in Table 5, the inducement of cerclage tension does not significantly change two-dimensional measures of mitral leaflet curvature and angulation with regard to the annulus, which reflect leaflet traction.

Cerclage induces conformational changes in the mitral valve annulus, as shown in Table 5. Mitral annular area (measured as a three-dimensional surface) falls with application of tension. Mitral annular geometry varies throughout the cardiac cycle. This cyclical annular contraction is preserved despite application of cerclage tension, which nevertheless reduces circumference and septal-lateral width. Annular height to commissure width ratio is increased by cerclage, which alters the annular saddle morphology. Tension acts to displace the posterior annulus caudally, towards the posterior papillary muscle.

TABLE 5

| | Baseline | Tension | p |
|---|---|---|---|
| Mitral leaflet configuration and traction | | | |
| Anterior leaflet angle with annulus ($\alpha$1, degrees) | 36.6 ± 6.4 | 34.0 ± 7.9 | 0.66 |
| Posterior leaflet angle with annulus ($\alpha$2, degrees) | 58.6 ± 21.5 | 72.2 ± 35.0 | 0.32 |
| Anterior leaflet curvature ($\beta$, degrees) | 145 ± 11 | 150 ± 9.0 | 0.14 |
| Mitral annular dynamics | | | |
| Mitral annular area (systolic, cm$^2$) | 7.0 ± 1.5 | 3.7 ± 1.2 | 0.01 |
| Mitral annular systolic contraction (%) | 13.1 ± 11.2 | 13.3 ± 7.2 | 0.98 |
| Annular height to commissure width ratio (%) | 27.0 ± 2.2 | 36.8 ± 3.9 | 0.02 |

Cerclage annuloplasty encircles both the mitral annulus and the left ventricular outflow tract, as shown in Table 6. Reciprocal constraint of these two structures during the cardiac cycle is observed when cerclage tension is applied. Whereas the cerclage diameter remains fixed throughout the cardiac cycle, the left ventricular outflow tract diameter enlarges during systole and contracts during diastole. Conversely, the constrained septal-lateral dimension of the mitral annulus is reduced by the left ventricular outflow tract during systole but not constrained during diastole. There is no gradient inducement across the left ventricular outflow tract using conventional fluid-filled catheters.

TABLE 6

| | | Baseline | Tension | p |
|---|---|---|---|---|
| Left ventricular outflow tract (LVOT) diameter | Systole | 2.1 ± 0.4 | 2.0 ± 0.4 | <0.05 |
| | Diastole | 1.9 ± 0.4 | 1.5 ± 0.4 | <0.01 |
| | Difference | 11% | 30% | <0.01 |
| Mitral valve annulus (MVA) diameter | Systole | 3.1 ± 0.5 | 2.5 ± 0.4 | <0.01 |
| | Diastole | 3.4 ± 0.6 | 2.9 ± 0.5 | <0.01 |
| | Difference | −10% | −14% | <0.01 |
| Combined LVOT and MVA | Systole | 5.2 ± 0.7 | 4.5 ± 0.6 | NS |
| | Diastole | 5.3 ± 0.9 | 4.4 ± 0.7 | NS |
| | Difference | −3% | 1% | NS |

This example demonstrates that the method for treating mitral valve regurgitation using an embodiment of the tensioning device according to the invention reduces mitral valve regurgitation.

All references, including publications, patent applications, and patents, cited herein are hereby incorporated by reference to the same extent as if each reference were individually and specifically indicated to be incorporated by reference and were set forth in its entirety herein.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for treating mitral valve regurgitation comprising:
forming a loop of suture around a mitral valve annulus;
coupling the suture with a lock, the lock including a locking enclosure and a locking pin, the locking pin having a first side, a second side, and having teeth on the first and second sides, the act of coupling including passing first and second ends of the suture through the locking enclosure and inserting the locking pin into the locking enclosure so that the first end of the suture engages with teeth on the first side of the locking pin and the second end of the suture engages with teeth on the second side of the locking pin;
holding the locking pin in an outer position by coupling the locking pin to an inner elongate shaft of a catheter;
pulling the inner elongate shaft of the catheter with respect to an outer tubular body of the catheter to pull the locking pin to the outer position;
maintaining the inner elongate shaft in place to hold the locking pin in the outer position;
adjusting tension of the suture to reduce mitral valve annulus size by moving the lock along the suture; and
locking tension of the suture around the mitral valve annulus by moving the pin from the outer position in which the teeth are disengaged from the suture and the lock is movable along the suture to an inner position in which the teeth are engaged with the suture and the lock is not movable along the suture,
wherein in the inner position the teeth of the lock are positioned within the locking enclosure.

2. The method according to claim 1, wherein the outer tubular body of the catheter includes a tube having a distal end and the locking enclosure includes a flange, and wherein the method further comprises advancing the lock within the tube until the flange abuts the distal end of the tube.

3. The method according to claim 2, wherein adjusting the tension of the suture by moving the lock along the suture includes pushing the catheter to move the lock along the suture to increase tension.

4. The method according to claim 2, wherein adjusting the tension of the suture by moving the lock along the suture further includes pulling the catheter to move the lock along the suture to decrease tension.

5. The method of claim 1, wherein the locking enclosure comprises a post member fixed at a distal end of the locking enclosure and extending from a first inside surface of the locking enclosure to a second, opposing inside surface of the locking enclosure, the post member maintaining separation between the first and second ends of the suture during the act of coupling the suture with the lock.

6. A method for treating mitral valve regurgitation comprising:
forming a loop of suture around a mitral valve annulus;
positioning two portions of the suture through a loop of a snare member, the snare member extending from a distal opening in an enclosure and mounted to a distal end of a moveable member mounted at least partially within a cavity of the enclosure;
adjusting tension of the suture to reduce mitral valve annulus size by moving the loop of the snare member along the suture; and
locking tension of the suture around the mitral valve annulus by moving the moveable member within the cavity and causing a portion of the loop to move into the enclosure through the distal opening, thereby reducing an effective diameter of the portion of the loop that extends out of the distal opening.

7. The method according to claim 6, wherein adjusting the tension of the suture includes pushing the moveable member to move the moveable member distally to increase the tension of the suture.

8. The method according to claim 6, wherein adjusting the tension of the suture further includes pulling the moveable member to move the movable member proximally to decrease the tension of the suture.

9. The method according to claim 6, wherein the moveable member includes a flange at a proximal end thereof.

* * * * *